United States Patent [19]

Blatch

[11] Patent Number: 4,689,181

[45] Date of Patent: Aug. 25, 1987

[54] FLUORINE-CONTAINING ORGANOSILANES USEFUL AS MAGNETIC MEDIA LUBRICANTS

[75] Inventor: Pamela E. Blatch, Midland, Mich.

[73] Assignee: Dow Corning Corporation, Midland, Mich.

[21] Appl. No.: 813,900

[22] Filed: Dec. 27, 1985

[51] Int. Cl.$^4$ .......................... C09F 7/00; C09F 7/08; C09F 7/18

[52] U.S. Cl. .................................. 260/408; 556/438; 556/442; 556/446; 428/447; 428/694; 428/695

[58] Field of Search ....................... 556/442, 438, 446; 428/447, 695, 694; 260/408

[56] References Cited

U.S. PATENT DOCUMENTS

| | | | |
|---|---|---|---|
| 3,450,738 | 6/1969 | Blocul | 556/446 X |
| 3,702,859 | 11/1972 | Pittman et al. | 556/438 |
| 4,007,313 | 2/1977 | Higuchi et al. | 428/447 |
| 4,308,212 | 12/1981 | Takamizawa et al. | 260/408 |
| 4,384,100 | 5/1983 | Takamizawa et al. | 556/438 X |
| 4,469,750 | 9/1984 | Fujiki et al. | 428/694 X |
| 4,469,751 | 9/1984 | Kobayashi | 428/447 |
| 4,501,801 | 2/1985 | Kimura et al. | 428/694 X |

FOREIGN PATENT DOCUMENTS 92428  6/1982 Japan ....................... 428/447

*Primary Examiner*—Paul F. Shaver
*Attorney, Agent, or Firm*—James E. Bittell

[57] ABSTRACT

The invention relates to new organosilanes represented by the following general formula:

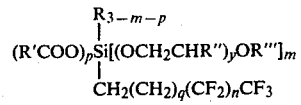

wherein R denotes a methyl, ethyl, propyl, or phenyl radical; R' denotes a monovalent hydrocarbon group having from 7 to 21 carbon atoms; R" denotes hydrogen or a methyl radical; R''' is selected from the class consisting of monovalent hydrocarbon groups having from 8 to 22 carbon atoms and acyl groups having from 8 to 22 carbon atoms; p has the value of 0, 1 or 2; m has the value of 1, 2, or 3; m+p has the value of 2 or 3; y has an average value from 1 to 20; n is a positive integer from 1 to 7; and q is a positive integer from 1 to 5. The use of the organosilanes as lubricants for magnetic recording media is described.

10 Claims, No Drawings

FLUORINE-CONTAINING ORGANOSILANES USEFUL AS MAGNETIC MEDIA LUBRICANTS

BACKGROUND OF THE INVENTION

The present invention relates to new fluorine-containing organosilanes and to their use to improve the lubricity and wear characteristics of magnetic recording media. More specifically, this invention relates to organosilanes having fluoroalkyl groups and acyloxypolyalkyleneoxy or alkoxypolyalkyleneoxy groups.

Magnetic recording media such as audio recording tapes, video recording tapes, and computer information recording disks must contact and often move across other machine parts during use. For instance, video tape moves across the magnetic head and through tape guides at high velocities in modern video tape recorders. Tapes suitable for these recorders must have good wear resistance and relatively low coefficients of friction if they are going to run smoothly and steadily for extended periods. If a tape has too high a coefficient of friction, it may vibrate when it passes through tape guides or over magnetic heads, so that recorded or reproduced signals are distorted from the originals. In some cases, a so-called "Q" sound due to vibration of the magnetic tape is encountered.

In order to reduce vibration and wear, efforts have been made to impart lubricity and smoothness to magnetic recording media. For example, polydimethylsiloxanes, castor oil, molybdenum disulfide, graphite, and higher fatty acids have been suggested as lubricants for magnetic recording tape. Such lubricants are often included in magnetic paint compositions so that the lubricant is mixed throughout the magnetic layer when the paint is applied to the recording media substrate. The extent of improved wear that can be obtained is however limited with these materials because when increased quantities are used in the magnetic layer, a phenomenon called "blooming" occurs. Blooming is caused by lubricating agent exuding out of the magnetic layer. When blooming occurs, the surface of the magnetic tape gets rough and the magnetic properties of the medium deteriorate rapidly. Consequently, there is a need for improved lubrication agents that will provide good lubricity and at the same time exhibit improved compatibility so that blooming does not occur.

U.S. Pat. No. 4,007,313 discloses the use in magnetic layers of organosilanes having the formula:

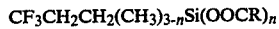

where R is a saturated or unsaturated aliphatic group, having from 7 to 17 carbon atoms, and n is an integer in the range of 1 to 3. It is taught that magnetic recording tape containing these silanes has a reduced coefficient of friction and improved wear resistance. Similarly, Japanese Patent O.P.I. No. 92,428 (1982) discloses magnetic recording media having a magnetic layer containing an organosilane of the formula:

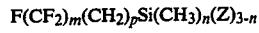

where Z is $R_fCOO-$, $R_fSO_3-$, or $R_fCOO(CH_2CH_2O)_k-$ with $R_f$ being defined as a saturated perfluoro hydrocarbon group having 1 to 20 carbon atoms, m is 1 to 20, n is 0 to 2, p is 2 to 20, and k is 1 to 50. The organosilane is said to improve abrasion resistance of magnetic media.

U.S. Pat. No. 4,308,212 discloses another class of organosilanes having the general formula:

where R is a monovalent hydrocarbon group having from 1 to 6 carbon atoms, R' is a monovalent hydrocarbon group having from 7 to 21 carbon atoms, n is a positive integer not exceeding 4 and m is a positive integer not exceeding 3. It is taught that these organosilanes can be applied to the surface of synthetic resins to improve their surface lubricity. Also, coating compositions containing synthetic resins are said to be improved by addition of these organosilanes.

Finally, U.S. Pat. No. 4,469,751 discloses still another class of organosilanes having the general formula:

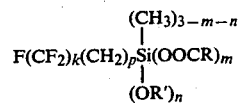

where R represents a saturated or unsaturated monovalent hydrocarbon group having from 7 to 21 carbon atoms, R' represents a saturated monovalent hydrocarbon group having from 1 to 4 carbon atoms, k is an integer of from 1 to 12, p is an integer of from 2 to 6, m is an integer of 1 or 2, and m is an integer of 1 or 2 provided that m+n is 3 or less. These organosilanes are described as lubricants for magnetic layers in recording media.

SUMMARY OF THE INVENTION

The present invention relates to new organosilanes represented by the following general formula:

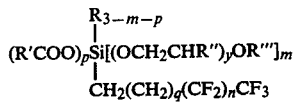

wherein R denotes a methyl, ethyl, propyl, or phenyl radical; R' denotes a monovalent hydrocarbon group having from 7 to 21 carbon atoms; R" denotes hydrogen or a methyl radical; R''' is selected from the class consisting of monovalent hydrocarbon groups having from 8 to 22 carbon atoms and acyl groups having from 8 to 22 carbon atoms; p has the value of 0, 1 or 2; m has the value of 1, 2, or 3; m+p has the value of 2 or 3; y has an average value from 1 to 20; n is a positive integer from 1 to 7; and q is a positive integer from 1 to 5. The invention also relates to improved magnetic recording media having a magnetic layer containing or coated with the new organosilanes of this invention.

DETAILED DESCRIPTION OF THE INVENTION

The new organosilanes of this invention are represented by general formula (I) above. In accordance with the formula, organosilanes of this invention have a fluoroalkyl group and at least one substituted alkyleneoxy group bonded to the silicon atom. The remaining valences of the silicon atom are filled by either hydrocarbon groups, acyloxy groups, or additional alkyleneoxy groups. The alkyleneoxy group may be an acyloxyalkyleneoxy, acyloxypolyalkyleneoxy, alkoxyalkyleneoxy or alkoxypolyalkyleneoxy radical.

More specifically, in formula (I), p has the value of 0, 1, or 2 and m has the value of 1, 2, or 3. The values of m and p are selected so that the sum of m and p has a value of 2 or 3. A hydrocarbon group denoted by R in formula (I) is bonded to the silicon atom by a carbon to silicon bond. Useful hydrocarbon groups are selected from the group consisting of methyl, ethyl, propyl, and phenyl. Generally, organosilanes where R denotes methyl are preferred because of their better stability and commercial availability. It is further preferred that the organosilanes have one methyl on silicon so that the value of m+p is 2.

In formula (I), R' denotes a monovalent hydrocarbon group having from 7 to 21 carbon atoms. The monovalent hydrocarbon groups may be saturated or unsaturated so that they may be selected from any of the alkyl or alkenyl radicals containing from 7 to 21 carbon atoms. For example, R' can be an alkyl radical such as heptyl, decyl, undecyl, tridecyl, pentadecyl, heptadecyl, and heneicosyl or an alkenyl radical such as heptenyl, decenyl, undecenyl, tridecenyl, pentadecenyl, heptadecenyl, and heneicosenyl. Generally, it is preferred that R' denote the hydrocarbon residue of a fatty acid. The tridecyl residue of myristic acid is most preferred.

R" denotes hydrogen or a methyl radical so that the substituted alkyleneoxy group in formula (I) can contain either ethyleneoxy units or propyleneoxy units with the ethyleneoxy units being preferred. The number of alkyleneoxy units represented by y can vary from 1 to 20, preferably from 4 to 15, in the silanes of this invention. The alkyleneoxy unit is capped by a group represented by R''' which can be either a monovalent hydrocarbon group having from 8 to 22 carbon atoms or an acyl group having likewise 8 to 22 carbon atoms. For example, R''' can be an alkyl radical such as octyl, 2-ethylhexyl, decyl, tetradecyl, hexyldecyl, and docosyl; an alkenyl radical such as octenyl, decenyl, 9-octadecenyl, docosenyl; a saturated acyl radical such as octanoyl, lauroyl, myristoyl, palmitoyl, and stearoyl; or an unsaturated acyl radical such as oleoyl, linoleoyl, and linolenoyl. It is preferred that R''' be an acyl radical derived from a fatty acid. Organosilanes where R''' is a mixture of saturated and unsaturated acyl radicals from Tall Oil acid having 16 or 18 carbon atoms are even more preferred.

The organosilanes of this invention also have a fluoroalkyl group bonded to silicon. It is believed that the fluoroalkyl portion of the silane molecule contributes significantly to reducing the surface energy of the magnetic layer and thereby improves greatly the smoothness and lubricity of magnetic recording media. In the fluoroalkyl group q can have a value from 1 to 5 and n can have a value from 1 to 7. For example, the fluoroalkyl group can be $CF_3CF_2CH_2CH_2-$, $CF_3(CF_2)_3CH_2CH_2-$, $CF_3(CF_2)_5(CH_2)_4-$, or $CF_3(CF_2)_7CH_2CH_2-$.

Any of the organosilanes of this invention can be used to improve the lubricity, wear, and abrasion characteristics of magnetic media. However, it has been found that organosilanes of the average formula

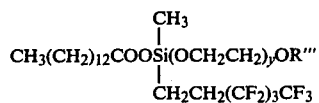

where y has a value of 4 to 15 and R''' denotes an acyl radical from a saturated or unsaturated fatty acid having 16 or 18 carbon atoms are especially effective in providing lubricity and reducing the stick-slip of magnetic media such as video recording tape.

The organosilanes of this invention can be synthesized in several ways. For example, a chlorosilane having a perfluoroalkyl substituent can be reacted with polyalkyleneoxide which is capped on one end with either an alkyl or acyl group. The reaction is typically carried out in the presence of a base such as pyridine which acts to trap the hydrogen chloride formed by the reaction. More specifically, organosilanes of formula (II) can be prepared by reacting the chlorosilane with an equimolar mixture of a fatty acid and the polyalkyleneoxide which is capped on one end.

Another way of preparing the organosilanes involves an interchange of short chain alkoxy groups on silicon with longer chain fatty acid and capped alkyleneoxide compounds. In this case, an alkoxysilane having a perfluoroalkyl substituent is reacted with an equimolar mixture of a fatty acid and the polyalkyleneoxide which is capped on on end. The reaction is carried out in the presence of acid or base catalyst and preferably with selective removal of the short chain alcohol as it is formed.

The organosilanes of this invention may be hydrolyzed by water under some conditions. However, hydrolysis is negligible in the absence of strong acid or base if normal care is taken to exclude water. It is believed that the bulky polyalkyleneoxide substituents on silicon contribute to the increased resistance of the organosilanes to hydrolysis. Irregardless, it has been found that magnetic recording tapes containing the organosilanes of this invention are sufficiently stable to the effects of atmospheric water vapor under normal conditions of use.

In another embodiment, the present invention relates to improved magnetic recording media having a nonmagnetic base and a magnetic layer formed thereon containing magnetizable particles dispersed in a resinous binder. The improved magnetic media are obtained by coating the magnetic layer with the organosilanes or by dispersing the organosilanes of this invention in the resinous binder of the magnetic layer. When dispersing the organosilanes within the magnetic layer, it is preferred to add from 0.2 to 10 and more preferably from 1 to 6 parts by weight of the organosilane for each 100 parts by weight of magnetic powder such as ferric oxide in the magnetic layer formulation.

Binders, magnetic particles, and other appropriate components for preparing magnetic media are well known. Examples of the magnetic particles include ferromagnetic iron oxide materials such as gamma-$Fe_2O_3$ and $Fe_3O_4$ with or without additional metals such as Co, Ni, and Mn, ferromagnetic metals such as Fe, Co, Ni, and alloys thereof such as Fe—Co, Fe—Ni, Co—Ni, and Fe—Co—Ni with or without other metals such as Al, Cr, Mn, Cu, and Zn. Magnetic particles are generally used in an amount of 200 to 800 parts by weight per 100 parts by weight of the binder which may vary somewhat depending on the type of recording medium as is well known in the art.

Binder resins can be thermoplastic or thermosetting. Typical thermoplastic resins used as binders include vinyl chloride-vinyl acetate copolymers, vinyl chloride-vinylidene chloride copolymers, acrylic ester-styrene copolymers, methacrylic ester-styrene copolymers, acrylic ester-vinylidene chloride copolymers, methacrylic ester-vinylidene chloride copolymers, urethane elastomers cellulose derivatives, and vinyl chloride-vinyl acetate-vinyl alcohol terpolymers. Examples of thermosetting resins used as binders include phenolic resins, melamine resins, alkyd resins, silicone resins, urea-formaldehyde resins, and mixtures of isocyanates and polyols. The binder resins may be used singly or in combination. Solvents used with the binder resins to prepare magnetic paints include aromatic compounds such as xylene, toluene, and benzene; ketones such as methyl ethyl ketone, methyl isobutyl ketone, cyclohexanone, and tetrahydrofuran; and mixtures thereof.

Other components, such as dispersion aids for the magnetic particles, carbon black, and aluminum oxide particles can also be used in the magnetic layer. Dispersion aids such as the polyoxyalkylene alkylphenylether phosphates are used to facilitate the initial dispersion of magnetic particles and to help prevent reagglomeration of the particles before the solidification of the resin on the substrate.

Magnetic recording media are usually manufactured by applying a magnetic paint composition to at least one side of a non-magnetic base. Drying and/or curing the coating then provides a magnetic layer on the base. The magnetic paints are prepared by dispersing binder resins, magnetic particles and other components in a solvent with a machine such as an Eiger ® mixer, ball mill, or a sand grinder. The organosilane lubricants of this invention can be added to the magnetic paint at any convenient time either before or after dispersion of the magnetic particles. The non-magnetic base may be in the form of a film, foil or sheet made of a variety of materials such as synthetic resins, metals, glasses, and ceramics. The recording media of the invention include video tapes, audio tapes, magnetic cards, magnetic disks, and the like.

Magnetic media containing the organosilane lubricants of this invention have improved wear characteristics, low coefficient of friction, and significantly reduced stick-slip tendencies. The extremely low stick-slip character of the magnetic media of this invention facilitates their smooth and steady movement so that vibration and associated distortion are reduced or eliminated.

The following examples are presented to furthr illustrate the invention and are not intended to limit the scope of the invention which is more fully delineated by the claims. In the examples, all parts are by weight unless otherwise specified.

EXAMPLE 1

This example shows the preparation of a silane of this invention. Polyoxyethylene (12) monooleate (40.5 g, 0.05 moles), myristic acid (11.4 g, 0.05 mole), pyridine (8.0 g, 0.10 mole), and toluene (150 g) were combined in a flask and heated to reflux under a nitrogen atmosphere. 3,3,4,4,5,5,6,6,6-nonafluorohexylmethyldichlorosilane (18.0 g, 0.05 mole) was continuously added to the flask over a 5 minute period. The mixture was refluxed for an hour. After cooling, the mixture was filtered to remove the pyridine hydrogen chloride that had formed. The filtrate was a 31.5% by weight solution in toluene of silane A represented by the following average formula:

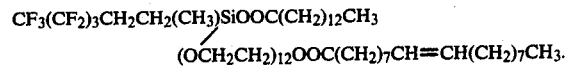

EXAMPLE 2

Silanes B, C, D, and E were prepared by the method of Example 1 using appropriate mixtures of the corresponding carboxylic acid and fatty acid glycol ester. Silanes B, C, D, and F are represented by the following average formulas:

Silane B

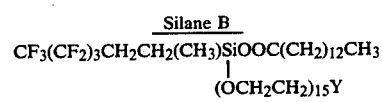

Silane C

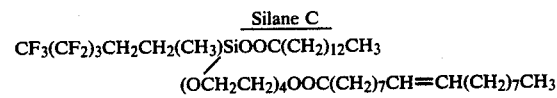

Silane D

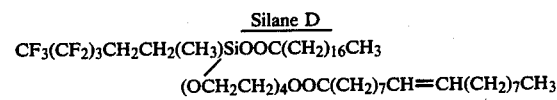

Silane E

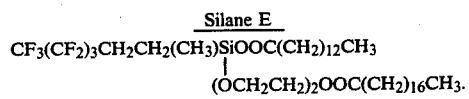

In the formula for Silane B, Y denotes the acyl radical from Tall Oil acid which is a natural mixture of saturated and unsaturated fatty acids with 16 to 18 carbon atom.

EXAMPLE 3

This example shows the preparation of a silane of this invention. Polyoxyethylene (4) monooleate (46.0 g, 0.10 mole), pyridine (8.0 g, 0.10 mole), and toluene (140.5 g) were combined in a flask and heated to reflux under a nitrogen atmosphere. 3,3,4,4,5,5,6,6,6-nonafluorohexylmethyldichlorosilane (18.0 g, 0.05 mole) was continuously added to the flask over a 5 minute period. The mixture was refluxed for 2 hours. After cooling, the mixture was filtered to remove the pyridine hydrogen chloride that had formed. The filtrate was a 24.2% by weight solution in toluene of silane F represented by the following average formula:

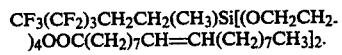

EXAMPLE 4

Silane G was prepared by the method of Example 3 using an alternative fatty acid glycol ester. Silane G is represented by the following average formula:

wherein Y denotes the acyl radical from Tall Oil acid which is a natural mixture of saturated and unsaturated fatty acids with 16 to 18 carbon atom.

EXAMPLE 5

This example shows the preparation of magnetic recording media containing the silane lubricants of this invention. Magnetic paint compositions containing the following components:

300 parts: Iron oxide particles with cobalt modified surface (average length 0.40 μm, average width 0.07 μm, cobalt content 3%, Pferrico ® 2566 supplied by Pfizer, Inc., Easton, Pa.)

72 parts: Polyester resin as 20% solution in tetrahydrofuran (viscosity for 15% resin in tetrahydrofuran 300 to 700 mPa.s, Estane ® 5701F-1 Resin supplied by B. F. Goodrich Company, Cleveland, Ohio)

15 parts: Polyoxyethylene (9) nonylphenylether phosphate as 25% solution in tetrahydrofuran (a mixture of mono and diphosphate esters of the polyethoxylated alkyl phenol, Gafac ® RE-610 supplied by GAF Corporation, Wayne, N.J.)

8.1 parts: Aluminum oxide powder (fractionated by sedimentation to less than or equal to 1 μm particles)

13.8 parts: Conductive carbon black 180 parts: Cyclohexanone 195 parts: Tetrahydrofuran 8.6 parts: Trimethylolpropane adduct of toluene diisocyanate as 75% solution in ethyl acetate (Mondur ® CB-75 supplied by Mobay Chemical Corporation, Pittsburgh, Pa.)

were prepared by ball milling, for 48 hours, a mixture of all the above components except for the polyisocyanate adduct. The polyisocyanate adduct and a silane lubricant were added to the milled mixtures just prior to coating the base film. Silane lubricants were added to the magnetic paint compositions at levels of either 2 or 6 parts per hundred parts of iron oxide particles. The magnetic paint composition was coated on polyester film (Mylar ®) at a thickness of 2 mils and cured for 30 minutes at 150° C.

The films were evaluated as magnetic tapes by determining the coefficient of friction, stick-slip amplitude, and wear properties. The films were cut into 0.5 inch strips and allowed to equilibrate, for at least 1 day, in a clean room at 23° C. and 48-52% relative humidity before testing.

The coefficient of friction (u) was measured by the following procedure. A strip of film was supported over an aluminum drum of diameter 6 cm, with a 100 g weight anchored on one end of the tape and the other end anchored to a load cell. The drum was rotated at 36 and 360 rpm for a period of 5 min at each speed and the output (load vs. time) recorded on an XY plotter. The coefficient of friction was calculated according to the following formula:

$$u = 1/\pi \ln(W_f/100)$$

where $W_f$ denotes the weight in grams measured by the load cell. All coefficient of friction values presented are averaged results of 4 to 6 trials for films coated with each magnetic paint composition.

The stick-slip amplitude is the degree of variance of the load in grams that occurs while the drum is rotated in the above described procedure for measuring the coefficient of friction.

Tape wear was determined by visual inspection of the films after performing the above test. The tape wear was compared by assigning a numeric rating from 1 to 3 with 1 denoting little or no burnishing, 2 denoting slight burnishing, and 3 denoting a high degree of burnishing.

The results obtained with a drum speed of 360 rpm are presented in Table 1. The data shows that the coefficient of friction and the stick-slip amplitude are reduced by the addition of silane lubricants to the magnetic paint composition. The data further shows that the stick-slip amplitude is unexpectedly reduced by Silanes A, B, C, D, and F relative to the use of comparison Silane H.

TABLE 1

| Lubricant Additive | | Coefficient | Stick-Slip | Wear |
| --- | --- | --- | --- | --- |
| Compound | Amount | of Friction | Amplitude | Rating |
| None (Control) | — | 0.779 | 30 | 3.0 |
| Myristic Acid* | 2 pph | 0.354 | 20 | 3.0 |
| Silane A | 2 pph | 0.367 | 7.5 | 1.7 |
| Silane B | 2 pph | 0.341 | 1.0 | 2.0 |
| Silane C | 2 pph | 0.350 | 5.0 | 2.5 |
| Silane D | 2 pph | 0.355 | 12.0 | 1.5 |
| Silane E | 2 pph | 0.379 | 16.0 | 1.5 |
| Silane F | 2 pph | 0.443 | 7.0 | 2.1 |
| Silane G | 2 pph | 0.503 | 20.0 | 3.0 |
| Silane H* | 2 pph | 0.323 | 15.0 | 3.0 |
| Silane I* | 2 pph | 0.503 | 10.0 | 2.0 |
| Silane B | 6 pph | 0.321 | 7.5 | 2.0 |
| Silane C | 6 pph | 0.359 | 26 | 2.0 |
| Myristic Acid* | 6 pph | 0.423 | 35 | 2.7 |
| Silane H* | 6 pph | 0.351 | 18.0 | 2.5 |

*Examples presented for comparison
Silane H is $CF_3(CF_2)_3CH_2CH_2(CH_3)Si[OOC(CH_2)_{12}CH_3]_2$
Silane I is $CF_3(CF_2)_3CH_2CH_2(CH_3)Si(OCH_2CH_2OC_4H_9)_2$ The results obtained with a drum speed of 36 rpm are presented in Table 2. The data shows that even at this low speed, the coefficient of friction and the wear ratings are reduced by the addition of silane lubricants to the magnetic paint composition. The date further shows that the stick-slip amplitude is unexpectedly reduced by Silane B relative to the use of comparison Silane H.

TABLE 2

| Lubricant Additive | | Coefficient | Stick-Slip | Wear |
| --- | --- | --- | --- | --- |
| Compound | Amount | of Friction | Amplitude | Rating |
| None (Control) | — | 0.718 | 20 | 3.0 |
| Myristic Acid* | 2 pph | 0.354 | 20 | 3.0 |
| Silane A | 2 pph | 0.590 | 50 | 1.0 |
| Silane B | 2 pph | 0.395 | 3 | 1.5 |
| Silane C | 2 pph | 0.450 | 10 | 1.5 |
| Silane D | 2 pph | 0.529 | 35 | 1.0 |
| Silane E | 2 pph | 0.501 | 20 | 1.1 |
| Silane F | 2 pph | 0.523 | 25 | 1 0 |
| Silane G | 2 pph | 0.499 | 23 | 1.0 |
| Silane H* | 2 pph | 0.522 | 10 | 2.0 |
| Silane I* | 2 pph | 0.553 | 20 | 1.2 |
| Silane B | 6 pph | 0.377 | 3.0 | 1.0 |
| Silane H* | 6 pph | 0.429 | 8.5 | 1.5 |
| Myristic Acid* | 6 pph | 0.424 | 5.5 | 1.5 |

*Examples presented for comparison
Silane H and I are the same as in TABLE 1.

EXAMPLE 6

This example illustrates the use of the silanes of this invention as a surface coating on magnetic media to reduce friction and wear. Magnetic paint composition of Example 5 without any added silane lubricant was coated on polyester film. The coated film was cut into strips and cured as described in Example 5. Lubricant was applied by dip-coating the strips in solution of Silane B to provide a topical lubricant coating of about 10 mg/m². The coefficient of friction, stick-slip amplitude, and wear ratings were determined for the film by the procedure described in Example 5 using a drum speed of 36 rpm. The results are presented in Table 3. The data shows that the coefficient of friction, stick-slip amplitude, and wear rating are reduced when the silane lubricant is applied to the surface of the cured magnetic coating. The data further shows that the coefficient of friction, stick-slip amplitude, and wear rating are unexpectedly lower with Silane B than with comparison Silane H.

TABLE 3

| Topical Lubricant | Coefficient of Friction | Stick-Slip Amplitude | Wear Rating |
|---|---|---|---|
| None (Control) | 0.718 | 20 | 3.0 |
| Silane B | 0.396 | 7.5 | 1.2 |
| Silane H* | 0.469 | 15.0 | 1.5 |
| Myristic Acid* | 0.647 | 40 | 1.7 |

*Examples presented for comparison
Silane H is the same as in TABLE 1.

What is claimed is:

1. An organosilane represented by the general formula,

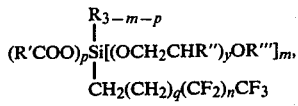

wherein R denotes a methyl, ethyl, propyl, or phenyl radical; R' denotes a monovalent hydrocarbon group having from 7 to 21 carbon atoms; R" denotes hydrogen or a methyl radical; R''' is selected from the class consisting of monovalent hydrocarbon groups having from 8 to 22 carbon atoms and acyl groups from fatty acids having from 8 to 22 carbon atoms; p has the value of 0, 1 or 2; m has the value of 1, 2, or 3; m+p has the value of 2 or 3; y has an average value from 1 to 20; n is a positive integer from 1 to 7; and q is a positive integer from 1 to 5.

2. The organosilane according to claim 1 wherein the monovalent hydrocarbon groups represented by the symbols R' and R''' are selected from the class consisting of alkyl groups and alkenyl groups.

3. The organosilane according to claim 2 wherein R denotes methyl, p is 1, and m is 1.

4. The organosilane according to claim 3 wherein R" is hydrogen, y has an average value of 10 to 20, and q is 1.

5. The organosilane according to claim 4 wherein R' is tridecyl and R''' is a mixture of saturated and unsaturated acyl groups having 16 or 18 carbon atoms.

6. In a magnetic recording medium having a nonmagnetic base and a magnetic layer formed thereon containing magnetizable particles dispersed in a resinous binder, the improvement comprising the magnetic layer having an organosilane represented by the formula

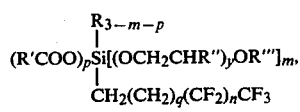

wherein R denotes a methyl, ethyl, propyl, or phenyl radical; R' denotes a monovalent hydrocarbon group having from 7 to 21 carbon atoms; R" denotes hydrogen or a methyl radical; R''' is selected from the class consisting of monovalent hydrocarbon groups having from 8 to 22 carbon atoms and acyl groups having from 8 to 22 carbon atoms; p has the value of 0, 1 or 2; m has the value of 1, 2, or 3; m+p has the value of 2 or 3; y has an average value from 1 to 20; n is a positive integer from 1 to 7; and q is a positive integer from 1 to 5, the organosilane being present in an amount sufficient to provide lubricating properties to the magnetic layer.

7. The magnetic recording medium according to claim 6 wherein the monovalent hydrocarbon groups represented by the symbols R' and R''' are selected from the class consisting of alkyl groups and alkenyl groups 8. The magnetic recording medium according to claim 7 wherein R denotes methyl, p is 1, and m is 1.

9. The magnetic recording medium according to claim 8 wherein R" is hydrogen, y has an average value of 10 to 20, and q is 1.

10. The magnetic recording medium according to claim 9 wherein R' is tridecyl and R''' is a mixture of saturated and unsaturated acyl radicals having 16 or 18 carbon atoms.

* * * * *